(12) United States Patent
Pareddy et al.

(10) Patent No.: US 11,389,094 B2
(45) Date of Patent: Jul. 19, 2022

(54) APPARATUS AND METHODS FOR INFANT MONITORING

(71) Applicant: Nemocare Wellness Private Limited, Hyderabad (IN)

(72) Inventors: Pratyusha Pareddy, Hyderabad (IN); Manoj Sanker P. R., Bangalore (IN)

(73) Assignee: Nemocare Wellness Private Limited, Hyderabad (IN)

(*) Notice: Subject to any disclaimer, the term of this patent is extended or adjusted under 35 U.S.C. 154(b) by 318 days.

(21) Appl. No.: 16/632,190

(22) PCT Filed: Jul. 16, 2018

(86) PCT No.: PCT/IB2018/055252
§ 371 (c)(1),
(2) Date: Jan. 17, 2020

(87) PCT Pub. No.: WO2019/016675
PCT Pub. Date: Jan. 24, 2019

(65) Prior Publication Data
US 2020/0163602 A1 May 28, 2020

(30) Foreign Application Priority Data
Jul. 17, 2017 (IN) .............................. 201741025396

(51) Int. Cl.
*A61B 5/1455* (2006.01)
*A61B 5/08* (2006.01)
*A61B 5/11* (2006.01)

(52) U.S. Cl.
CPC ........ *A61B 5/14552* (2013.01); *A61B 5/0826* (2013.01); *A61B 5/1116* (2013.01);
(Continued)

(58) Field of Classification Search
CPC . A61B 5/0205; A61B 5/02055; A61B 5/1455; A61B 5/14551; A61B 5/14552; A61B 5/14532; A61B 5/14542; A61B 5/14546; A61B 5/024; A61B 5/02411; A61B 5/02416; A61B 5/02427; A61B 5/02433; A61B 5/02438; A61B 5/02444; A61B 5/1116; A61B 5/1118;
(Continued)

(56) References Cited

U.S. PATENT DOCUMENTS 5,555,891 A * 9/1996 Eisenfeld ............... A61B 5/486
600/595
5,720,284 A * 2/1998 Aoyagi .............. A61B 5/14551
600/309

(Continued)

FOREIGN PATENT DOCUMENTS

EP           0850013 B1    2/2004

*Primary Examiner* — Chu Chuan Liu
(74) *Attorney, Agent, or Firm* — The Webb Law Firm

(57) ABSTRACT

The present invention relates to infant monitoring equipment, and particularly relates to apparatuses and methods for non-invasive monitoring and tracking of infants' vital health parameters, and for raising alerts on prediction or detection of one or more predefined health conditions. The invention provides apparatuses, methods and computer program products for non-invasive monitoring of blood analytes in a subject, and in particular embodiments, in infants.

14 Claims, 14 Drawing Sheets

(52) U.S. Cl.
    CPC . *A61B 2503/045* (2013.01); *A61B 2560/0204* (2013.01); *A61B 2562/0219* (2013.01); *A61B 2562/0271* (2013.01)

(58) Field of Classification Search
    CPC ... A61B 5/0826; A61B 5/746; A61B 2503/04; A61B 2503/045; A61B 2562/0219
    See application file for complete search history.

(56) References Cited

U.S. PATENT DOCUMENTS

| | | | |
|---|---|---|---|
| 6,104,938 A | 8/2000 | Huiku et al. | |
| 2004/0039297 A1 | 2/2004 | Abreu | |
| 2006/0258921 A1* | 11/2006 | Addison | A61B 5/726 600/323 |
| 2011/0004072 A1* | 1/2011 | Fletcher | A61B 5/6804 600/300 |
| 2013/0276785 A1* | 10/2013 | Melker | A61M 16/026 128/204.23 |

* cited by examiner

APPARATUS AND METHODS FOR INFANT MONITORING

CROSS-REFERENCE TO RELATED APPLICATIONS

This application is the U.S. national phase of International Application No. PCT/IB2018/055252 filed Jul. 16, 2018, and claims priority to Indian Provisional Patent Application No. 201741025396 filed Jul. 17, 2017, the disclosures of which are hereby incorporated by reference in their entirety.

FIELD OF THE INVENTION

The present invention relates to infant monitoring equipment, and particularly relates to apparatuses and methods for non-invasive monitoring and tracking of infants' vital health parameters, and for raising alerts on prediction or detection of one or more predefined health conditions.

BACKGROUND

Infants generally, and premature babies in particular are susceptible to a variety of life threatening conditions (the most common being apnea, respiratory distress, sepsis and hypothermia). Busy hospital settings create situations where these conditions can often go unnoticed or detected late, with the potential for causing irreversible injury to the newborn or death. Management and prevention of such situations is possible with accurate and continuous monitoring systems. Existing monitoring solutions suffer from multiple drawbacks including being too expensive for low-resource settings, too bulky and unsuitable for continuous monitoring and have a high rate of false alarms, which forces health care providers to either ignore the alarms or to visually monitor the babies (both of which can have undesirable outcomes) highly unreliable.

Likewise when a newborn is brought home, the family is instructed to keep a close eye on the vitals of the baby—but are unable to do so in a consistent or reliable manner. Both parents and health care providers therefore require an efficient solution for monitoring and babies' health and well-being—and for detecting life threatening conditions such as hypothermia, apnea, sudden infant death syndrome, blue baby syndrome and respiratory distress.

The present invention seeks to provide solutions to all of the above, by presenting an accurate, cost effective, compact apparatus for infant monitoring, with related methods for configuration and operation.

SUMMARY

The present invention relates to infant monitoring equipment, and particularly relates to apparatuses and methods for non-invasive monitoring and tracking of infants' vital health parameters, and for raising alerts on prediction or detection of one or more predefined health conditions. The invention provides apparatuses, methods and computer program products for non-invasive monitoring of blood analytes in a subject, and in particular embodiments, in infants.

In a first embodiment, the invention presents a method for non-invasive monitoring of blood analytes. The method comprises the steps of (i) receiving at one or more photodetectors, electromagnetic waves that have been emitted from one or more illumination sources and have passed through a subject's skin and tissue prior to being received at said one or more photodetectors, and based on the electromagnetic waves received at said one or more photodetectors, determining at least one of (a) a first value comprising a peripheral capillary oxygen saturation (SpO2) value corresponding to the subject, wherein said determination of the first value is based on a ratio of (1) reflectance or absorbance readings obtained from infrared spectrum wavelengths, to (2) reflectance or absorbance readings obtained from red spectrum wavelengths, (b) a second value comprising a carboxyhaemoglobin (HbCO) value corresponding to the subject, wherein said determination of the second value is based on a ratio of (3) reflectance or absorbance readings obtained from green spectrum wavelengths, to (4) reflectance or absorbance readings obtained from at least one of red and infrared spectrum wavelengths, (c) a third value comprising a methaemoglobin (HbMe) value corresponding to the subject, wherein said determination of the third value is based on a ratio of (5) reflectance or absorbance readings obtained from orange spectrum wavelengths, to (6) reflectance or absorbance readings obtained from at least one of red and infrared spectrum wavelengths, and (d) a fourth value representing the total hemoglobin level of the subject, wherein said fourth value is determined based on the first, second and third values.

In an embodiment of the method, the fourth value is the sum of (i) the first value multiplied by a first coefficient, (ii) the second value multiplied by a second coefficient and (iii) the third value multiplied by a third coefficient.

In another embodiment, the method may include determining a fifth value representing presence of bilirubin in the subject's blood, wherein said fifth value is based on a ratio of (i) reflectance or absorbance readings obtained from blue spectrum wavelengths, to (ii) reflectance or absorbance readings obtained from at least one of red and infrared spectrum wavelengths.

The method may additionally include determining a heart rate of the subject based on the electromagnetic waves received at said one or more photodetectors, wherein determination of the heart rate is based on a measured elapsed time between received wavelength peaks. In another embodiment, the method may include the step of determining a respiratory rate corresponding to the subject, wherein determining said respiratory rate comprises (i) converting a reflectance or absorbance waveform received at the one or more photodetectors into frequency domain, and (ii) determining the subject's respiratory rate based on the frequency domain data.

In an embodiment of the method (i) the infrared spectrum wavelengths include wavelengths between 840 nm to 960 nm, (ii) the red spectrum wavelengths include wavelengths between 550 nm and 690 nm, (iii) the green spectrum wavelengths include wavelengths between 530 nm and 675 nm, and (iv) the orange spectrum wavelengths include wavelengths between 600 nm and 660 nm.

In a further embodiment, the blue spectrum wavelengths include wavelengths between 455 nm and 485 nm.

In a particular method embodiment, one or more of the red, infrared, green and orange wavelengths may be emitted from a first illumination source, and the blue spectrum wavelengths are emitted from a second illumination source.

The invention additionally provides an apparatus for non-invasive monitoring of blood analytes. The apparatus comprises a sensing apparatus, said sensing apparatus comprising (i) a first illumination source—photodetector pair, comprising a first illumination source and a first photodetector, wherein said first photodetector is configured to receive electromagnetic waves that have been emitted from the first illumination source and that have passed through a subject's skin and tissue prior to being received at said first photodetector, and (ii) a processor configured to determine based on the electromagnetic waves received at least at said first photodetector, at least one of (a) a first value comprising a peripheral capillary oxygen saturation (SpO2) value corresponding to the subject, wherein said determination of the first value is based on a ratio of (1) reflectance or absorbance readings obtained from infrared spectrum wavelengths, to (2) reflectance or absorbance readings obtained from red spectrum wavelengths, (b) a second value comprising a carboxyhaemoglobin (HbCO) value corresponding to the subject, wherein said determination of the second value is based on a ratio of (3) reflectance or absorbance readings obtained from green spectrum wavelengths, to (4) reflectance or absorbance readings obtained from at least one of red and infrared spectrum wavelengths, (c) a third value comprising a methaemoglobin (HbMe) value corresponding to the subject, wherein said determination of the third value is based on a ratio of (5) reflectance or absorbance readings obtained from orange spectrum wavelengths, to (6) reflectance or absorbance readings obtained from at least one of red and infrared spectrum wavelengths, and (d) a fourth value representing the total hemoglobin level of the subject, wherein said fourth value is determined based on the first, second and third values.

In an embodiment of the apparatus, the fourth value is the sum of (i) the first value multiplied by a first coefficient, (ii) the second value multiplied by a second coefficient and (iii) the third value multiplied by a third coefficient.

The apparatus may include a second illumination source—photodetector pair, comprising a second illumination source and a second photodetector, wherein said second photodetector is configured to receive electromagnetic waves that have been emitted from the second illumination source and that have passed through a subject's skin and tissue prior to being received at said second photodetector. In an embodiment of the apparatus, the processor may be configured to determine a fifth value representing presence of bilirubin in the subject's blood, wherein said fifth value is based on a ratio of (i) reflectance or absorbance readings obtained from blue spectrum wavelengths at the second photodetector, to (ii) reflectance or absorbance readings obtained from at least one of red and infrared spectrum wavelengths received at the first photodetector.

The processor may additionally be configured to determine a heart rate of the subject based on the electromagnetic waves received at a photodetector within said apparatus, wherein determination of the heart rate is based on a measured elapsed time between received wavelength peaks. Further, the processor may be configured to determine a respiratory rate corresponding to the subject, wherein determining said respiratory rate comprises (i) converting a reflectance or absorbance waveform received at a photodetector within the apparatus into frequency domain, and (ii) determining the subject's respiratory rate based on the frequency and time domain data.

In embodiments of the apparatus, (i) the infrared spectrum wavelengths include wavelengths between 840 nm to 960 nm, (ii) the red spectrum wavelengths include wavelengths between 550 nm and 690 nm, (iii) the green spectrum wavelengths include wavelengths between 530 nm and 675 nm, and (iv) the orange spectrum wavelengths include wavelengths between 600 nm and 660 nm. In a further embodiment, the blue spectrum wavelengths may include wavelengths between 455 nm and 485 nm.

In a specific embodiment of the apparatus, one or more of the red, infrared, green and orange wavelengths are emitted from a first illumination source, and the blue spectrum wavelengths are emitted from a second illumination source.

The sensing apparatus may additionally be configured to include one or more of one or more thermistors, a motion detection sensor, a battery and power management controller, a wireless transceiver, and a haptic feedback generator.

The sensing apparatus may be configured to adaptively control the number of reflectance or absorbance wavelength samples that are (i) pulsed by illumination source(s) within the sensing apparatus, (ii) received by photodetector(s) within the sensing apparatus and (iii) processed by the processor.

The sensing apparatus may also be configured to modify the number of reflectance or absorbance wavelength samples that are (i) pulsed by illumination source(s) within the sensing apparatus, (ii) received by photodetector(s) within the sensing apparatus and (iii) processed by the processor, based on one or more of (a) determination of a distress state or an abnormal state associated with the subject, and (b) determination of a low charge state associated with a battery within the sensing apparatus.

In an embodiment, the sensing apparatus may be configured such that one or both of red and infrared wavelengths are pulsed by illumination source(s) within the sensing apparatus at a higher frequency than the frequency at which one or more of green, orange and blue wavelengths are pulsed by illumination source(s) within the sensing apparatus.

The invention additionally includes a computer program product for non-invasive monitoring of blood analytes. The computer program product comprises a non-transitory computer usable medium having computer readable program code embodied therein, said computer readable program code comprising instructions for (i) receiving at one or more photodetectors, electromagnetic waves that have been emitted from one or more illumination sources and have passed through a subject's skin and tissue prior to being received at said one or more photodetectors, and based on the electromagnetic waves received at said one or more photodetectors, determining at least one of (a) a first value comprising a peripheral capillary oxygen saturation (SpO2) value corresponding to the subject, wherein said determination of the first value is based on a ratio of (1) reflectance or absorbance readings obtained from infrared spectrum wavelengths, to (2) reflectance or absorbance readings obtained from red spectrum wavelengths, (b) a second value comprising a carboxyhaemoglobin (HbCO) value corresponding to the subject, wherein said determination of the second value is based on a ratio of (3) reflectance or absorbance readings obtained from green spectrum wavelengths, to (4) reflectance or absorbance readings obtained from at least one of red and infrared spectrum wavelengths, (c) a third value comprising a methaemoglobin (HbMe) value corresponding to the subject, wherein said determination of the third value is based on a ratio of (5) reflectance or absorbance readings obtained from orange spectrum wavelengths, to (6) reflectance or absorbance readings obtained from at least one of red and infrared spectrum wavelengths, and (d) a fourth value representing the total hemoglobin level of the subject, wherein said fourth value is determined based on the first, second and third values.

BRIEF DESCRIPTION OF THE ACCOMPANYING DRAWINGS

Figure 6:
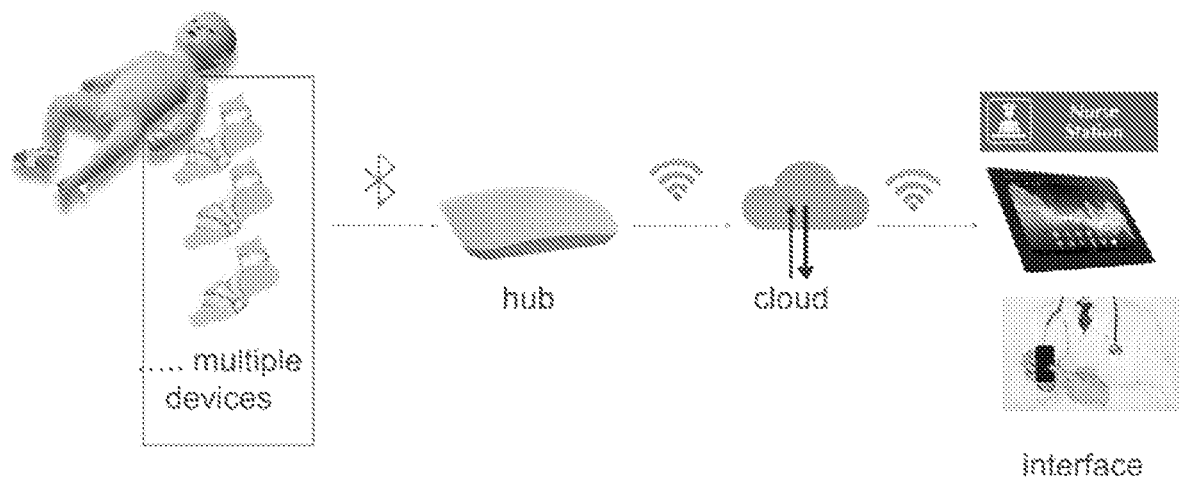
Figure 7:
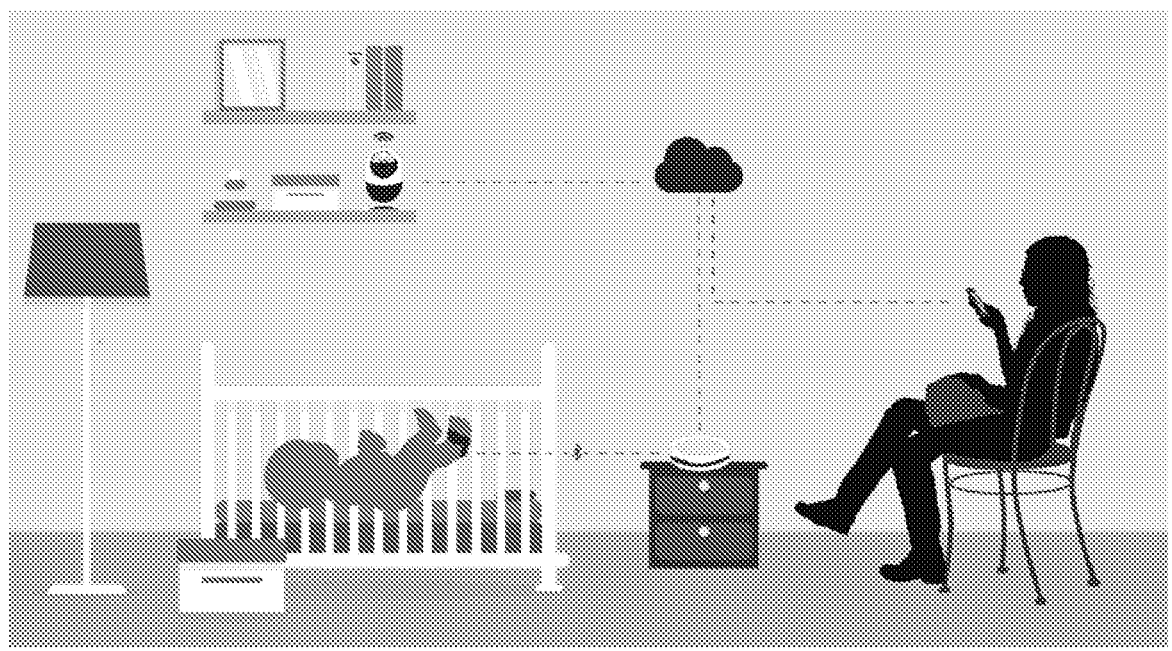

FIGS. 6 and 7 respectively illustrate implementations of the apparatus of the present invention in a clinical environment and in a home environment.

Figure 8:
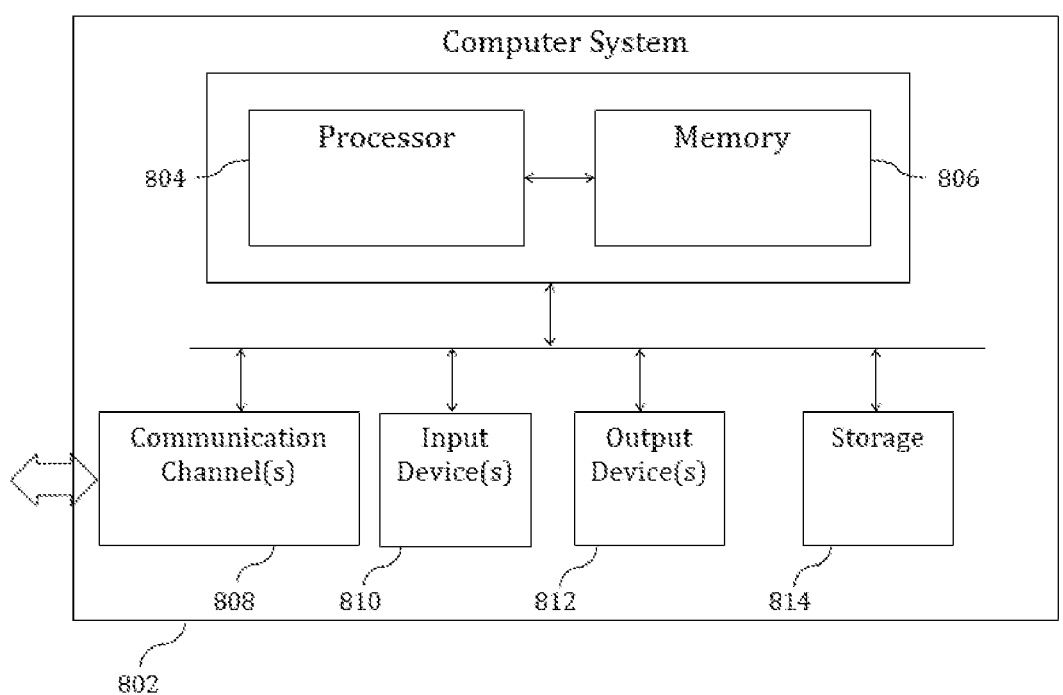

FIG. 8 illustrates and exemplary computer system configured to implement one or more embodiments of the present invention.

DETAILED DESCRIPTION

The present invention addresses several of the above described needs in the state of art, by providing systems, methods, and apparatus that wirelessly monitor the health of a baby. In particular, at least one implementation of the present invention monitors a child's blood oxygen level and indicates an alert when an abnormal trend is identified.

The present invention includes a system for wirelessly monitoring the health of an infant. The system can comprise a sensing apparatus removably disposed within a wearable housing. The sensing apparatus can include a processing unit configured to non-invasively receive health parameters from one or more sensors and to process said health parameters. A wireless transceiver can also be in communication with the processing unit. The wireless transmitter can be configured to transmit the processed health readings to a receiving station. Any of the system, wearable housing and sensing apparatus may be configured to indicate an alarm if the processed health readings indicate a health trend that falls outside of a particular threshold. In certain embodiments, the sensing apparatus itself may include hardware components configured to administer corrective steps in response to particular alarm events.

Additional features and advantages of the invention will be set forth in the description which follows, and in part will be obvious from the description, or may be learned by the practice of the invention. These and other features of the present invention will become more fully apparent from the following description, or may be learned by the practice of the invention as set forth hereinafter.

Figure 1:
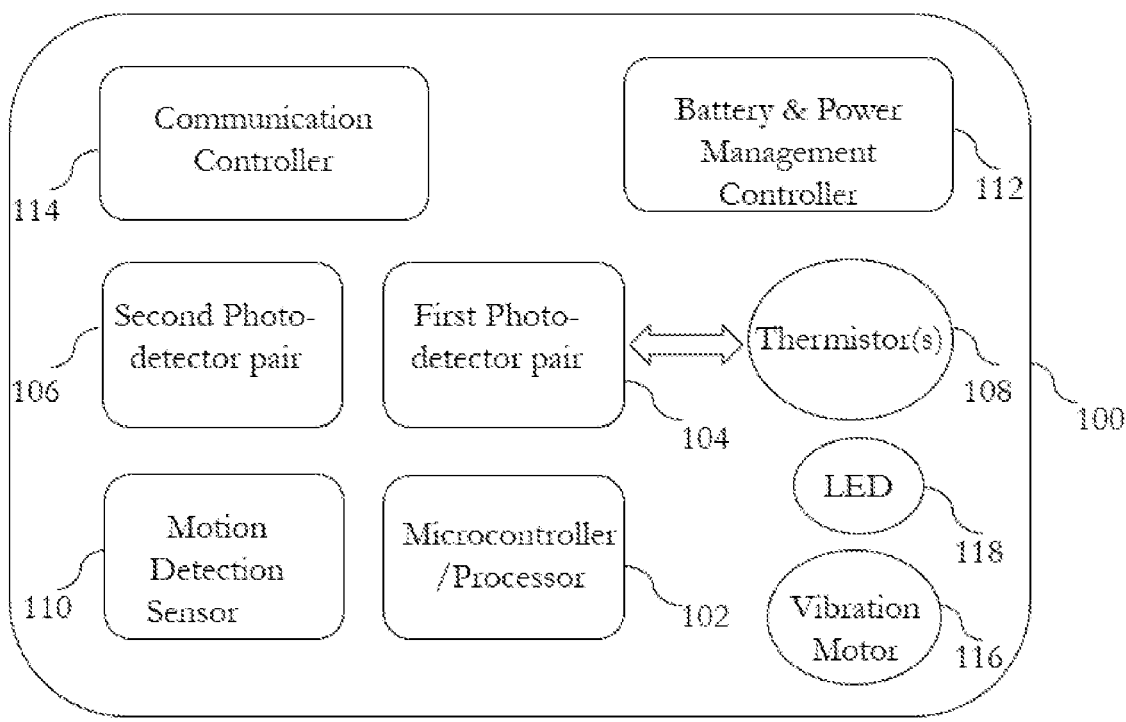
FIG. 1 illustrates a block diagram of a sensing apparatus and components there within.

FIG. 1 illustrates a sensing apparatus in accordance with an embodiment of the present invention.

The sensing apparatus 100 of FIG. 1 includes (i) a processor or microcontroller 102, (ii) a first illumination source—photodetector pair 104, (iii) an optional second illumination source 106 comprising photodetector pair L2, (iv) one or more thermistors 108 (v) motion detection sensor 110, (v) a battery and power management controller 112, (vi) a communication controller 114, (vii) a vibration motor 116 (or other haptic feedback generator), (viii) one or more indicator LEDs 118 and, (ix) one or more audio alarms on device (not shown in FIG. 1) Each of the components of the sensing apparatus are discussed in more detail below.

The sensing apparatus 100 is configured to implement photoplethysmogram (PPG) based measurements and readings using pulse oximetry. In an embodiment of the invention, the sensing apparatus 100 uses reflectance pulse oximetry. However, it would be understood that transmittance pulse oximetry may be implemented in other embodiments of the invention.

First illumination source—photodetector pair 104 comprises (i) a first illumination source capable of generating a plurality of wavelengths within a plurality of predefined wavelength ranges, and (ii) a corresponding first photodetector configured to receive wavelengths that have been emitted from the first illumination source 104, passed through the subject's skin and reflected off from subcutaneous tissue and bone. The first illumination source may comprise any of a broad spectrum illumination source capable of simultaneously emitting all of the predefined wavelengths (for example an incandescent light source), an illumination source capable of emitting specific wavelength ranges based on the input current or voltage (for example a variable output LED), or a plurality of illumination sources, each configured to emit a certain sub-set of wavelengths within the plurality of predefined wavelengths. The first photodetector may be a single photodetector configured to detect the plurality of predefined wavelengths emitted from the first illumination source, or may comprise a plurality of photodetectors, each configured (for example by disposition of appropriate band pass filters) to detect a sub-set of wavelengths within the plurality of predefined wavelengths emitted by the first illumination source.

In a preferred embodiment of the invention, first illumination source—photodetector pair 104 comprises a single illumination source capable of emitting different wavelength ranges based on varying input currents or input voltages, and a single photodetector capable of detecting emitted wavelengths across the entire emission spectrum of first illumination source. In a more preferred embodiment the distance between the first illumination source and corresponding photodetector are separated by a distance of between 2 mm and 12 mm, and in a preferred embodiment, are separated by a distance of 8 mm.

In an embodiment of the invention, the first illumination source is configured to emit at least one of (and preferably all of) the following discrete ranges of wavelengths:

Between 840 nm to 960 nm, more preferably between 870 nm and 900 nm, and optimally a peak emission wavelength of 880 nm (infrared spectrum).

Between 550 nm to 690 nm, more preferably between 650 nm and 670 nm (red wavelengths), and optimally a peak emission wavelength of 660 nm, Between 530 nm to 575 nm, and optimally a peak emission wavelength of 537 nm (green wavelengths), Between 600 nm to 660 nm, (orange wavelengths), and Optionally, between 455 nm and 485 nm (blue wavelengths).

Figure 2A:
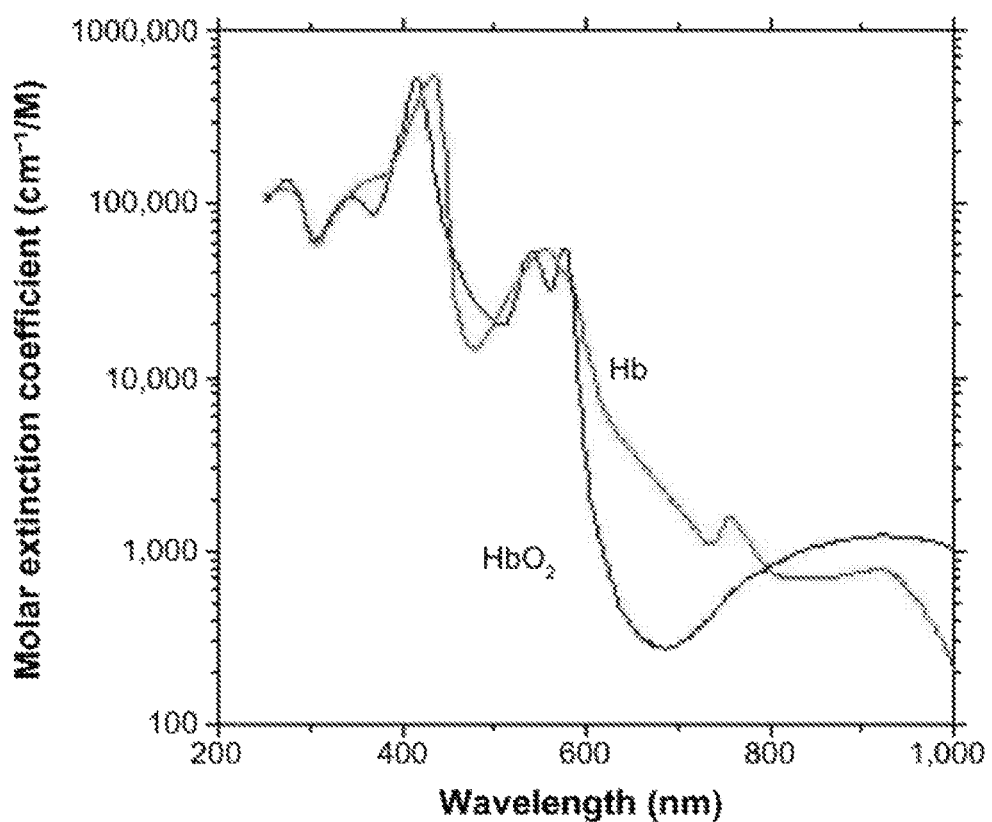
FIGS. 2A and 2B illustrate the absorption spectra of haemoglobin components.
Figure 2B:
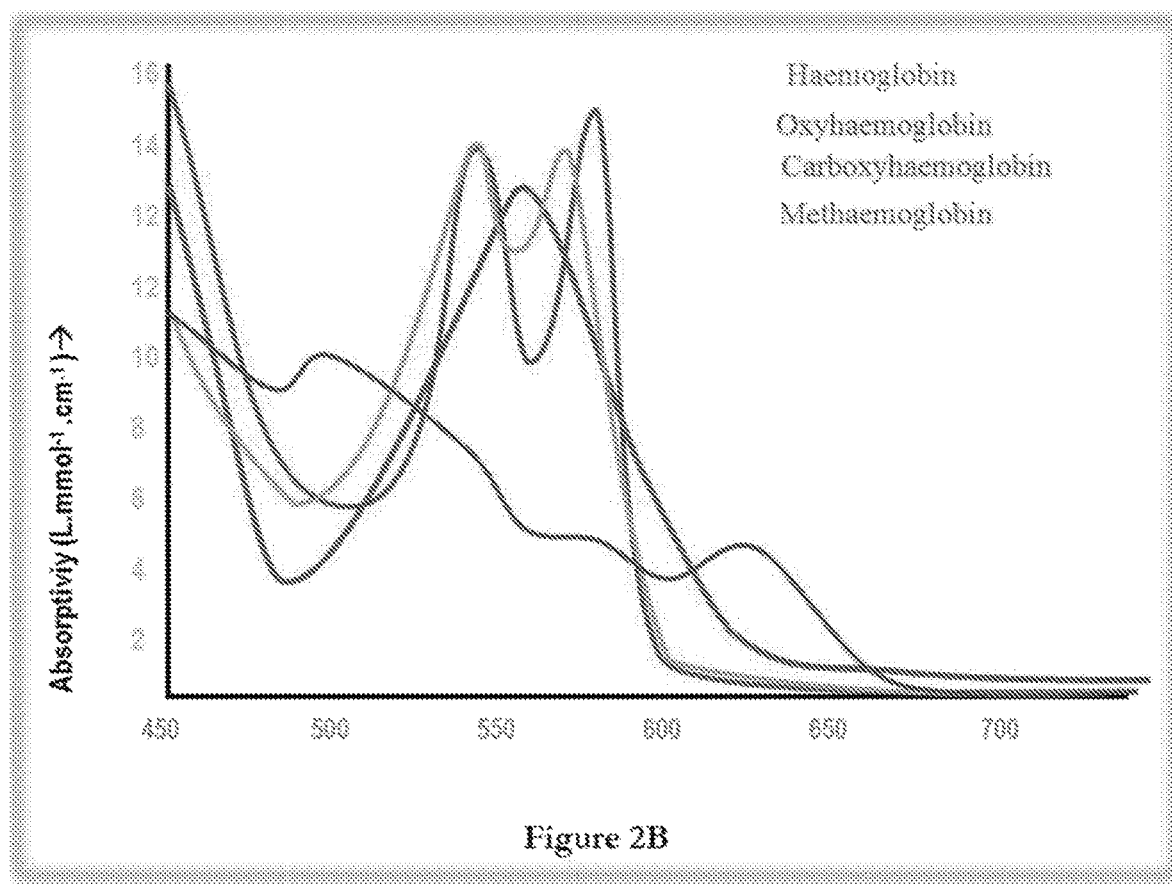

FIGS. 2A and 2B illustrate the absorption spectra of haemoglobin components, including haemoglobin (Hb), oxyhaemoglobin (Hb02), carboxyhaemoglobin (HbCO), and methaemoglobin (HbMe). Based on the absorption spectra, and to ensure that the sensing apparatus is capable of correctly correlating the impact of each haemoglobin component on the reflected wavelengths received at the photodetector within the first illumination source photodetector pair 104, the processor/microcontroller 102 within sensing apparatus 100 may be configured to:

Determine a first value comprising a peripheral capillary oxygen saturation (Sp02) value based on a ratio of reflectance or absorbance readings corresponding to the infrared and red spectrum emissions from the first illumination source.

Determine a second value corresponding to presence of carboxyhaemoglobin (HbCO), based on a ratio of reflectance or absorbance readings corresponding to (i) the green spectrum emissions and (ii) one of the red and infrared spectrum emissions (preferably the infrared emissions) from the first illumination source.

Determine a third value corresponding presence of methaemoglobin (HbMe), based on a ratio of reflectance or absorbance readings corresponding to (i) the orange spectrum emissions and (ii) one of the red and infrared spectrum emissions (preferably the infrared emissions) from the first illumination source.

Determine a value for the total haemoglobin level in the subject, based on the calculated first, second and third values. In an embodiment, each of the first second and third values is multiplied by predefined first, second and third coefficients respectivelywherein the first coefficient is a predefined coefficient corresponding to Sp02, the second coefficient is a predefined coefficient corresponding to carboxyhaemoglobin, and the third coefficient is a predefined coefficient corresponding to methaemobglobin. In an embodiment, the total haemoglobin level is calculated as the sum of the first value multiplied by the first coefficient, the second value multiplied by the second coefficient and the third value multiplied by the third coefficient. The calculated total haemoglobin level enables a determination whether the subject is anemic or has low perfusion, and depending on whether the subject is anemic, alarm thresholds for various health conditions may be modified for more accurate condition monitoring, to raise alarms, and to reduce the rate of false alarms.

Determine a heart rate of the subject based on the reflectance received at the first photodetector, by detecting wavelength peaks or troughs in the reflected emission readings or the emission absorbance readings, and determining the elapsed time between the wavelength peaks), which elapsed time corresponds to the subject's heart rate.

Determine a respiratory rate of the subject, based on the reflectance detected at the first photodetector, which determination comprises converting the received reflectance waveform or the received emission absorbance waveform into the frequency domain, and using the frequency domain data to determine a respiratory rate. This is discussed in more detail below.

Optionally determine a fourth value corresponding to presence of bilirubin, based on a ratio of reflectance or absorbance readings corresponding to (i) the blue spectrum emissions and (ii) one of the red and infrared spectrum emissions (preferably the infrared emissions) from the first illumination source.

Figure 3:
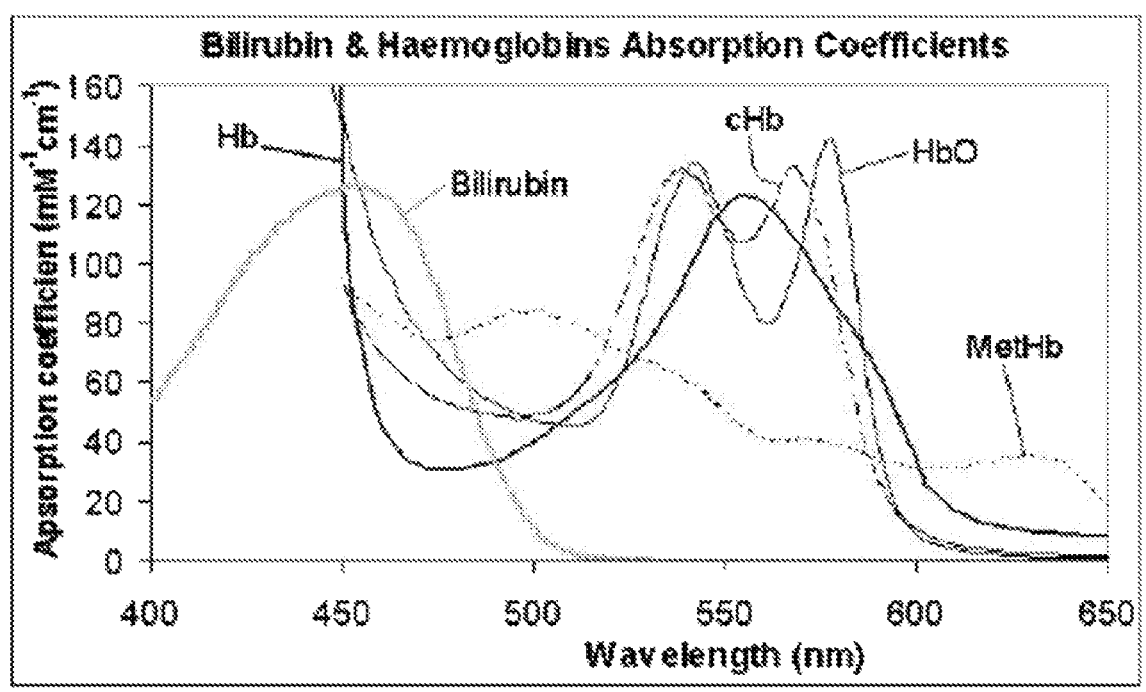
FIG. 3 illustrates the absorption spectrum of bilirubin compared with the haemoglobin spectrum.

It would be understood that the selection of illumination spectrums for detection of haemoglobin, oxyhaemoglobin, carboxyhaemoglobin, methaemoglobin and transcutaneous bilirubin, and the values of coefficients used for determining total haemoglobin levels in accordance with the above description may be based on the respective absorption spectra illustrated in FIGS. 2A, 2B and 3.

In an embodiment of the invention, the first illumination source is positioned substantially at the center of the sensing apparatus 100.

In an optional embodiment, the sensing apparatus 100 includes a second illumination source photodetector pair 106 comprising (i) a second illumination source capable of generating wavelengths in the 455 nm and 485 nm (blue wavelengths) range and (ii) a corresponding second photodetector configured to receive wavelengths that have been emitted from the second illumination source, passed through the subject's skin and reflected off from subcutaneous tissue and bone. In this embodiment, the processor or microcontroller 102 may be configured to determine a value corresponding to presence of bilirubin in the subject's blood, based on a ratio of reflectance readings corresponding to (i) the blue spectrum emissions and (ii) one of the red and infrared spectrum emissions (preferably the infrared emissions) from the first illumination source.

In an embodiment, the sensing apparatus 100, or the wearable housing in which the sensing apparatus 100 is configured to be disposed, provides light shielding components to ensure that illumination from light sources other than the first illumination source/second illumination source (for example ambient light) is shielded from the corresponding photodetector(s) thereby eliminating generation of false signals at said photodetectors.

In an embodiment of the present invention, the sensing apparatus 100 includes at least a first thermistor 108, positioned such that in use, the first thermistor 108 is in contact with or in the vicinity of a subject's skin (for example in contact with the skin on the dorsal region of the subject's foot, or for example in contact with the skin on the plantar region of the subject's foot). The processor/microcontroller 102 may be configured to use data or signals from the first thermistor 108 to determine the subject's temperature, and to arrive at a determination whether the subject is suffering from hypothermia or hyperthermia. In one embodiment, the first thermistor 108 is positioned at least 3 mm away from the first illumination source or the second illumination source (or both) to ensure that temperature readings from the thermistor are unaffected by thermal radiation emitted from the corresponding illumination sources.

In an embodiment of the invention, the sensing apparatus 100 may additionally include a second thermistor (not shown), positioned such that in use, the second thermistor is not in contact with or in the vicinity of the subject's skin, and is instead positioned to provide temperature readings of the surrounding environment. The temperature readings from the second thermistor may be used to normalize/rationalize the readings from the first thermistor and to avoid false positives or false alarms, by determining whether temperature changes detected at the first thermistor are influenced by temperature changes in the surrounding environment. In an embodiment, the first and second thermistors are positioned on opposite surfaces of the sensing apparatus. In a further embodiment, one or both of the first and second thermistors may comprise negative temperature coefficient (NTC) type thermistors or may comprise of temperature sensing Integrated Circuits (ICs).

The motion detection sensor 110 may comprise one or more of an accelerometer (for example an MEMS accelerometer) and a gyroscope. The data from the motion detection sensor 110 is input to a kalman filter—which is used to identify body positions and relative movements of the subject. The data from the kalman filter may then be used (i) for noise filtration purposes and (ii) for data compensation, to ensure that motion/posture related artefacts (or signals) do not lead to false alarms or faulty pulse signals. Data from the motion detection sensor may also be used to identify sleeping patterns of babies, and in certain embodiments to identify (based on posture) instances of kangaroo mother care (KMC) to enable correlations between occurrence of KMC and corresponding changes in vital signs of the baby (for example, temperature, heart rate, respiration rate, perfusion index, heamodynamics etc.).

In a particular embodiment of the invention, data from the sensing apparatus 100 may be correlated with data from a camera to further cross-check, filter noise, and detect false alarms by accounting for motion/posture related artefacts and other environmental artefacts.

The battery and power management controller 112 manage the power supply to the sensing apparatus 100, enable recharging of batteries, and generates alerts in case charge falls below a predefined threshold. In an embodiment, battery and power management controller 112 may include a dedicated temperature sensor that tracks the temperature of the battery and shuts off the power when there is overheating—which is an indication of malfunction.

The communication controller 114 within sensing apparatus 100 may comprise any communication controller configured to transmit data over a wired line or wirelessly from the sensing apparatus to a desired network location, for display, storage, remote access and/or further processing. In an embodiment the communication controller may be configured for wi-fi, infrared, wireless, Bluetooth, Bluetooth Low Energy (BLE) or ANT+ or NFC or ZigBee or LoRa based transmission.

The sensing apparatus 100 may also include one or more indicator LEDs 118 configured to provide visual alerts responsive to occurrence of one or more predefined events.

The sensing apparatus 100 may additionally include a vibration motor 116 and/or any other haptic feedback generator which may be configured to generate haptic feedback in response to detection of apnea or other distress like situations in babies. Haptic feedback (for example through a vibration motor 116) is capable of being sensed by the baby, and would provide stimulation to the baby—resulting in the baby recommencing breathing in apnea-type situations.

Figure 4:
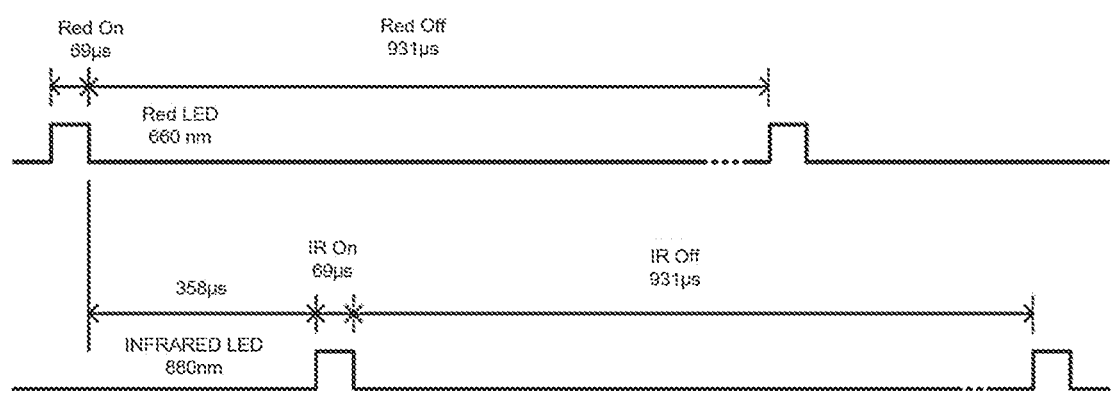
FIG. 4 illustrates an exemplary sampling pattern using red and infrared wavelengths for measuring SpO2.

FIG. 4 illustrates the triggering of illumination pulses from the illumination sources for the purposes of reflectance based oximetry. While a higher number of samples (pulses) provides higher accuracies, it also results in a drain on power resources. In some embodiments, the power management software may be configured to switch between different modes where in a first mode, the sensing apparatus obtains a larger number of samples per unit time, while in a second mode, the sensing apparatus obtains a smaller number of samples per unit time. The selection of an appropriate sampling mode may be based on a predefined set of rules. In an embodiment, the sensing apparatus may obtain a larger number of samples per unit time where a distress event or abnormal event has been detected, and may obtain a smaller number of samples per unit time where no abnormality is detected. In another embodiment, the number of samples obtained may depend on the power reserves left in the battery.

In an embodiment of the invention, the red and infrared wavelengths are pulsed from the illumination source(s) at a higher frequency—as these are required to measure SpO2 and heart rate—which can change significantly over short periods of time. Since carboxyhaemoglobin, methaemoglobin and bilirubin values change more slowly, the frequency of green, orange and blue wavelength pulses may be relatively lower.

As illustrated in FIG. 4, the pulsing of different wavelengths may be staggered—and the intervals between successive pulses of a particular range of wavelengths may be selected to ensure that sufficient time is provided to obtain peak reflectance of that wavelengths, while ensuring that successive pulses are close enough together to detect real time changes in content of the various haemoglobin components.

In an embodiment, photodetector data, and data from other sensors may be communicated to the processor/microcontroller 102 in data samples that are each 32 bits long or 16 bit or higher based on constraints.

Figure 5A:
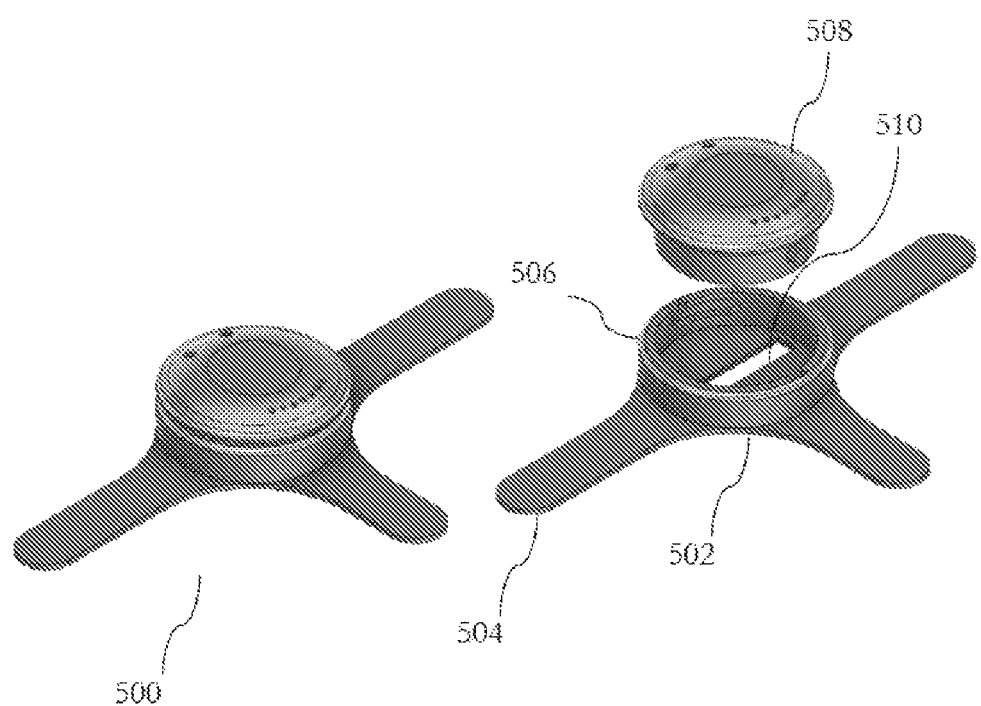
FIG. 5A to 5I illustrate embodiment of a wearable monitoring device comprising a wearable housing and a sensing apparatus, along with components thereof.

FIG. 5A illustrates an embodiment of the wearable monitoring device 500 comprising the wearable housing 502 and a sensing apparatus 508 configured to engage with said wearable housing 502. In various embodiments, the wearable housing 502 may comprise a wearable article that is selectively removeable from the subject.

In a preferred embodiment of the invention, the sensing apparatus 508 is configured for being placed adjacent to or in contact with a subject or a baby's foot, on one of the dorsal surface or the plantar surface. It has been found that significant advantages may be had by positioning the sensing apparatus 508 such that the illumination source(s) and corresponding photodetector(s) are substantially aligned with the dorsal artery of the foot. Accordingly in an invention embodiment, the wearable housing 502 is designed for being affixed to a subject's foot such that when the sensing apparatus 508 is correctly housed within (or engaged with) the wearable housing 502, the illumination source(s) and corresponding photodetector(s) are substantially aligned with the dorsal artery of the foot.

In the embodiment illustrated in FIG. 5A, wearable housing 502 comprises a plurality of straps 504 (or any other anatomy appropriate fastener) to affix the wearable housing 502 securely to a corresponding portion of the subject's anatomy (e.g. foot, forehead, sternum etc.). In an embodiment of the invention, instead of or in addition to the illustrated straps 504, the surface of wearable housing 50 that is in contact with the subject's skin may be coated with a medical/bio-appropriate/skin-friendly adhesive. Wearable housing 502 additionally includes a housing compartment 506 configured to securely house sensing apparatus 508. One or both of housing compartment 506 and sensing apparatus 508 may include fasteners to ensure secure removable engagement between housing compartment 506 and sensing apparatus 508 (for example, a threaded arrangement, snap fit arrangement, snap-lock arrangement or interference fit arrangement). In an embodiment of the invention, wearable housing 502 may include an additional thermistor on a surface of the housing that is intended to be in contact with the subject's skin. In one embodiment, the thermistor in wearable housing 502 and the thermistor within sensing apparatus 508 are respectively positioned such that, when sensing apparatus 508 is securely deployed within wearable housing 502 and said wearable housing 502 is positioned for operation on a subject's foot, one of the thermistor in wearable housing 502 and the thermistor in sensing apparatus 508 is in contact with skin on the dorsal side of the foot, while the other of the thermistor in wearable housing 502 and the thermistor in sensing apparatus 508 is in contact with skin on the plantar side of the foot. Since the temperatures on the plantar side and dorsal side are typically different from each other, the temperature readings obtained from both sides can be used for a variety of different applications, including refining checks for hyperthermia or hypothermia, prevention of false alarms, generation of more complete data points etc.

As illustrated in FIG. 5A, the base of housing compartment 506 may additionally include one or more apertures 510—positioned such that when the sensing apparatus 508 is securely positioned within housing compartment 506 for operation, one or more of (i) the first illumination source—photodetector pair 104, (ii) the second illumination source—photodetector pair 106 and (iii) the first thermistor 108 positioned to be in contact with the subject's skin—are positioned on top of said one or more apertures—to ensure that the housing compartment 506 does not interfere with operation of the illumination sources, photodetectors and/or thermistors.

In a specific embodiment, the wearable housing 502 may include an alignment feature configured to conform to a specific portion of the human anatomy, such that when the wearable housing 502 is positioned such that the alignment feature is positioned in conformance with the corresponding anatomical feature, the illuminations source(s) and corresponding photodetector(s) of sensing apparatus 508 that is securely positioned within wearable housing 502 are aligned with the dorsal artery of the foot.

In an embodiment of the invention, the wearable housing 502 and the sensing apparatus 508 are configured to interface such that the illumination source-photodetector pairs L1/L2, thermistor configured for being in contact with the subject's skin and optionally the haptic feedback generator are all positioned proximal to the dorsal surface or the plantar surface of the subject's foot. In an embodiment, wearable housing 502 is made with medical grade material and soft fabric and will be designed to fit snugly and unobtrusively on the child's foot for prolonged wear without any allergies.

In an embodiment, each wearable housing 502 may include a unique identifier (for example an RFID tag, NFC or passive RFID tag, chip or microchip) that enables the sensing apparatus 508 to uniquely recognize said wearable housing 502—and to record or generate historical information corresponding to each unique housing that the sensing apparatus 508 is used with—for example, the number of days that a wearable housing 502 has been in use, to ensure that the wearable housing 502 is periodically changed to avoid rashes or allergies arising out of use beyond the prescribed expiry date. In a further embodiment, sensing apparatus 508 may include sensors for checking for or detecting the unique identifier of a wearable housing 502 to which the sensing apparatus 508 is mated. In an embodiment, the processor/microcontroller of the sensing apparatus 508 may be configured to partially or fully disable sensing apparatus 508 in the event it is mated to a wearable housing 502 that fails to satisfy one or more predefined requirements, which one or more predefined requirements may be ascertained based on the presence and/or content of the unique identifier disposed within said wearable housing 502.

Figure 5B:
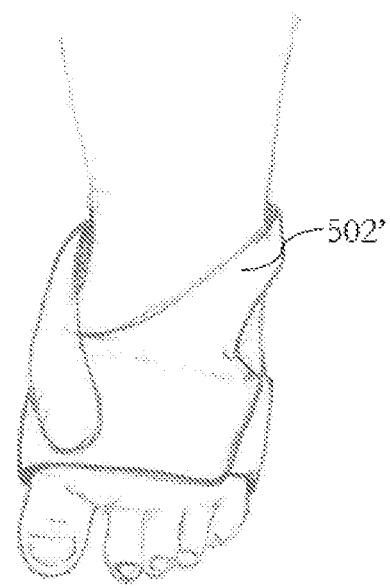
Figure 5C:
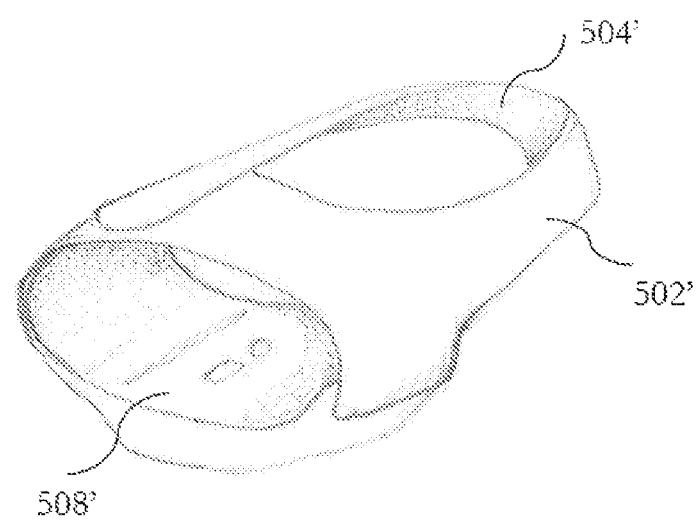

FIGS. 5B to 5I illustrate alternate embodiments of the wearable monitoring device 500 comprising a wearable housing 502' and a sensing apparatus 508' configured to engage with said wearable housing 502'. In the embodiment of FIG. 5B, the wearable housing 502' comprises a wearable article that is selectively removeable from the subject. In the illustrated embodiment wearable housing 502' comprises an appropriately shaped wrap or sock that wraps around an infant's foot. As shown in more detail in FIG. 5C, the wearable housing 502' includes straps 504' that enable said wearable housing 502' to be wrapped around the infant's foot and secured in place. Wearable housing 502' is configured such that sensing apparatus 508' can be placed and secured within a pocket or flap inside wearable housing 502' such that, when wearable housing 502' is disposed about the infant's foot, sensing apparatus 508' is positioned at an appropriate location with respect to the infant's foot to enable the functionality envisaged and discussed above.

In a preferred embodiment of the invention, the wearable housing 502' is configured such that when secured within wearable housing 502', sensing apparatus 508' is placed adjacent to or in contact with a subject or a baby's foot, on one of the dorsal surface or the plantar surface—and in a particular embodiment, such that the illumination source(s) and corresponding photodetector(s) are substantially aligned with the dorsal artery of the foot.

In an embodiment, each wearable housing 502' may include a unique identifier (for example an RFID tag, NFC or passive RFID tag, chip or microchip) that enables the sensing apparatus 508' to uniquely recognize said wearable housing 502'—and to record or generate historical information corresponding to each unique housing that the sensing apparatus 508' is used with—for example, the number of days that a wearable housing 502' has been in use, to ensure that the wearable housing 502' is periodically changed to avoid rashes or allergies arising out of use beyond the prescribed expiry date. In a further embodiment, sensing apparatus 508' may include sensors for checking for or detecting the unique identifier of a wearable housing 502' to which the sensing apparatus 508' is mated. In an embodiment, the processor/microcontroller of the sensing apparatus 508' may be configured to partially or fully disable sensing apparatus 508' in the event it is mated to a wearable housing 502' that fails to satisfy one or more predefined requirements, which one or more predefined requirements may be ascertained based on the presence and/or content of the unique identifier disposed within said wearable housing 502'.

Figure 5D:
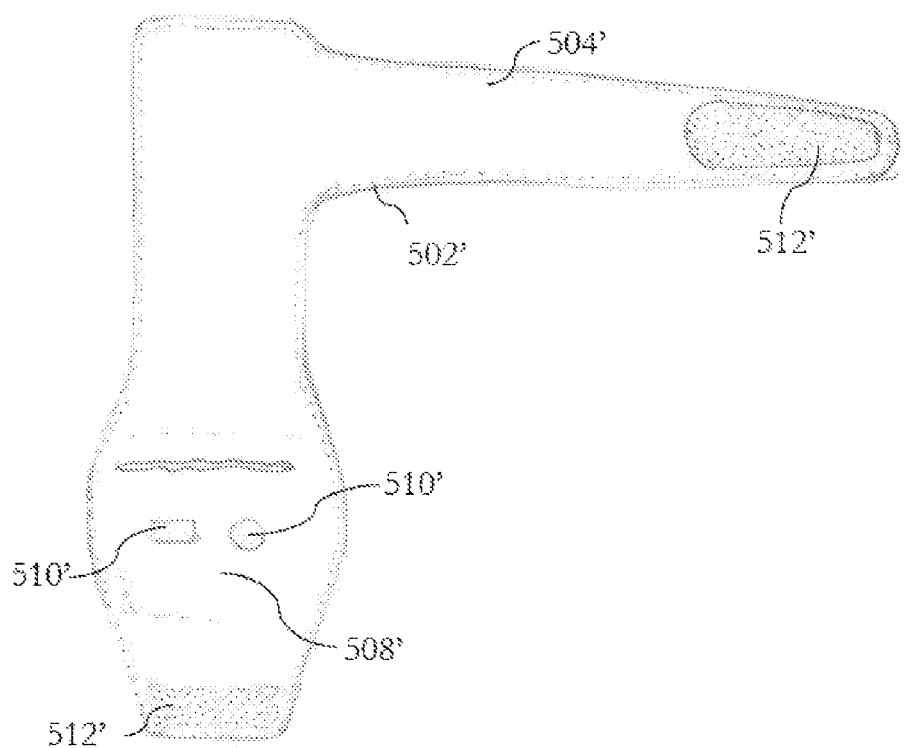

FIG. 5D illustrates the wearable housing 502' in an unwrapped configuration, comprising a substantially L-shaped configuration, wherein said wearable housing 502' includes a plurality of apertures 510', that permit for an illumination source—photodetector pair and/or a thermistor to obtain blood analyte data and/or temperature data corresponding to the infant while sensing apparatus 508' is secured within wearable housing 502'. Wearable housing 502' is additionally provided with one or more Velcro strips, adhesive patches or other fasteners or means for affixing or fastening said wearable housing onto an infant's foot.

Figure 5E:
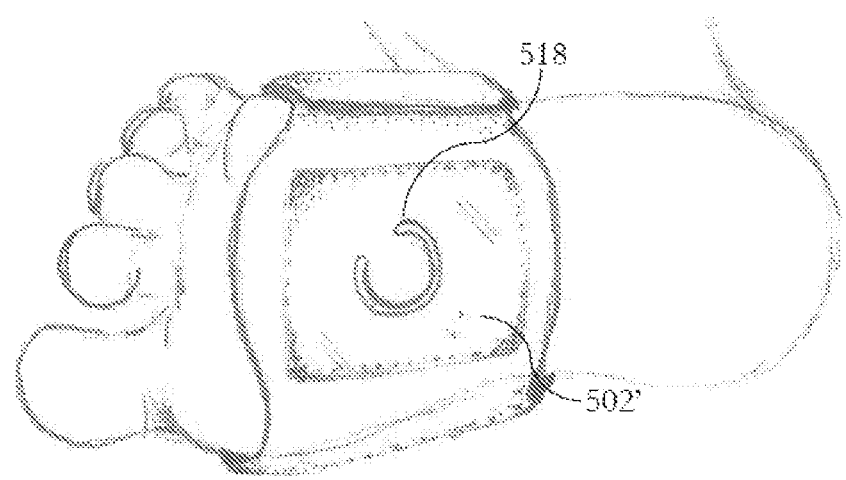
Figure 5F:
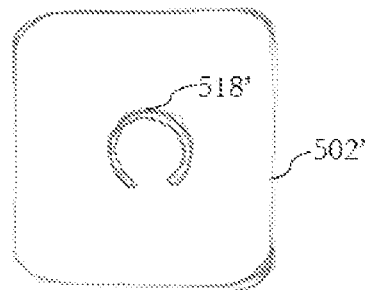
Figure 5G:
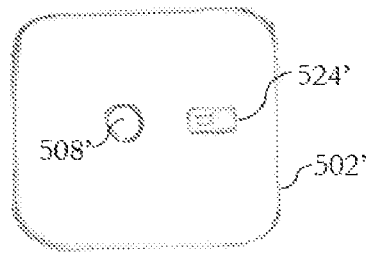
Figure 5H:
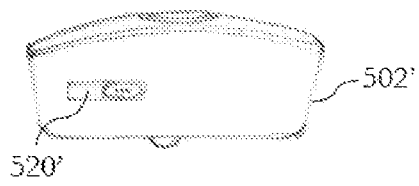
Figure 5I:
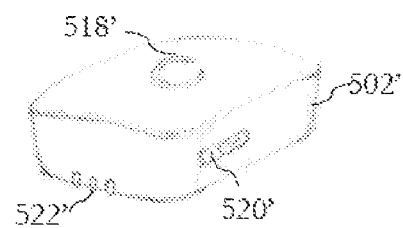

FIG. 5E illustrates the sole of an infant's foot to which the wearable housing 502' has been applied—and in which the sensing apparatus 508' has been positioned such that it is positioned beneath the sole of the infant's foot. In the illustrated embodiment, wearable housing 502' includes at least one aperture through which an LED 518 on wearable housing 502' is visible.

FIGS. 5F to 5I respectively illustrate top, bottom side and perspective views of sensing apparatus 508'—wherein said sensing apparatus 508' includes LED 518', at least one power switch 520', thermistor 522', one or more illumination sources—photodetector couples 524', and electrical contacts 526 to enable sensing apparatus 508' to interface with a charger/power source.

FIG. 6 illustrates implementation of one or more apparatuses in accordance with the teachings of the present invention in a clinical environment—wherein a plurality of the apparatuses are each applied to a specific subject—and are in wireless communication with a wireless access point or hub which wireless access point is used to communicate data from each of the sensing apparatus through a communication network/cloud and to one or more of a nursing station, computing device, display device or other user interface that is accessible by a health care provider. In an embodiment, the system may be enable a health care provider to selectively or simultaneously access data generated by the plurality of sensing apparatus.

FIG. 7 illustrates an implementation of an apparatus in accordance with the teachings of the present invention in a home environment wherein data from the sensing apparatus and/or wearable housing, and data from a camera that is tracking movements of the infant/subject is communicated over a communication network/cloud to a computing device, display device or other user interface that is accessible by the home care provider (e.g. parent or caregiver).

Exemplary Features of Method for Determining Heart Rate

In an exemplary embodiment of the invention, the method for determining heart rate comprises:

PPG cycle peak detection (peaks above a dynamic threshold after removing near by peaks).

DC component e.g., absorption due to skin bones and other constants are removed by calculating the mean and removing from each data point 4 point moving average taken to smoothen values, Dynamic threshold for minimum consideration of peaks is calculated from data samples.

Peaks detected and corresponding locations in terms of sample points are recorded, this location of peaks is used to calculate inter beat interval in terms of number of samples.

This information is converted to heart rate using the formula heart rate=sampling frequency×60/inter beat interval samples. This value in terms of number of beats per minute. The information is also used to calculate other parameters like Heart Rate Variability using individual inter beat intervals.

Exemplary Features of Method for Determining SpO2

In an exemplary embodiment of the invention, the method for determining SpO2 comprises:

Both red and IR data samples are used.

Location of peaks from the heart rate derivation discussed above is used.

The method relies on the ratio between AC component of IR and RED and DC component of IR and RED.

Exemplary Features of Method for Determining Respiration Rate

In an exemplary embodiment of the invention, the method for determining respiration rate comprises extracting the dominant frequency from the PPG signal using autoregressive models of different order along with frequency estimation techniques based on wavelet transforms or other equivalent transforms to determine dominant respiratory frequency in 3 respiratory induced variation-frequency, amplitude and intensity steps. The method may include:

Preprocessing using time domain segmentation method.

Extracting respiratory component-identification of peaks and troughs Estimating respiratory rate and arriving at a consolidated or fused or normalized estimated value.

Quality assessment.

Advantages offered by the apparatus and methods of the present invention

The apparatus and methods of the present invention have been found to offer at least the following advantages over the prior art:

novel sensor array consisting of LEDs of required wavelength, motion sensor, thermistor and vibration motors, capable of determining 4 or more health parameters (including heart rate, respiration rate, SpO2, temperature, haemoglobin, heart rate variability, Perfusion Index, transcutaneous bilirubin and body position) all from a single device, results are capable of being visualised using one or more displays, provides methods for detecting apnea and other causes of distress using detected heart rate, respiration rate and SpO2, thereby reducing false alarms, in a home setting data from a camera is also used to make detections more accurate.

eliminates cases of low perfusion due to cases like hypothermia, anemia or more.

can be configured to generate audio/visual/buzzer alerts on detection of distress conditions, enables stimulation of baby on detection of apnea or other cases of distress using vibration motors or haptic engine, the device can be used at multiple physiological sites such as foot, forehead chest etc.

data from the device can be used to quantify and correlate Kangaroo Mother Care related data.

machine learning based methods may additionally be used for prediction of apnea and thereby enabling early stimulus of the baby as a preventive step.

device includes an adhoc communication module—where device and communication module can be detached for power saving and can still work independently.

enables network configuration such that close to 40 devices can be monitored on a single tablet/web Interface through the wireless access point or networking hub illustrated in FIG. 6.

enables automatic recognition of babies—using vitals baseline models as biometric identity.

enables creation of health record from day one, which can be synced seamlessly with hospital data and health care system.

enables detection of whether device is worn by the baby.

enables data correction of SpO2 using accelerometer, gyroscope (MPU/IMU) data to remove motion artefacts.

enables determination of respiration rate calculated from band worn on foot.

same hardware device can be used and upgraded with custom software modules to check for different disease states.

enables integration of camera data with pulse ox, motion sensors and audio to generate holistic data and reduce false alarms.

interlocking mechanism of the consumable adhesive patch and the sensor module enables replacement of wearable housing and re-use of the sensing apparatus.

Aids in promoting interventional activities like breast feeding owing to its wireless and truly portable nature.

Enables any bed to be converted into an ICU bed owing to its high accuracy and reliability of the system.

The hub allows multiple devices to be connected to the central monitoring station. In an embodiment, each wearable housing may include a unique identifier (for example an RFID tag, passive RFID tag, chip or microchip) that enables the sensing apparatus to uniquely recognize said wearable housing—and to record or generate historical information corresponding to each unique housing that the sensing apparatus is used with—for example, the number of days that a wearable housing has been in use, to ensure that the wearable housing is periodically changed to avoid rashes, infection or allergies arising out of use beyond the prescribed expiry date.

provides capabilities such as GPS to track baby's whereabouts using blue tooth beacon technology. can include open APIs for seamless integration into any Hospital IT/Electronic Health Record (EHR) system. the device and its system are designed to quantify Kangaroo Mother Care and track its implementation. It will be an important marker to understand and track the usage of the device. the device can be configured using over the air updates and updated as well.

FIG. 8 illustrates an exemplary computer system 802 for implementing the present invention.

The illustrated system comprises computer system 802 which in turn comprises one or more processors 804 and at least one memory 806. Processor 804 is configured to execute program instructions—and may be a real processor or a virtual processor. It will be understood that computer system 802 does not suggest any limitation as to scope of use or functionality of described embodiments. The computer system 802 may include, but is not be limited to, one or more of a general-purpose computer, a programmed microprocessor, a micro-controller, an integrated circuit, and other devices or arrangements of devices that are capable of implementing the steps that constitute the method of the present invention. Exemplary embodiments of a computer system 802 in accordance with the present invention may include one or more servers, desktops, laptops, tablets, smart phones, mobile phones, mobile communication devices, tablets, phablets and personal digital assistants. In an embodiment of the present invention, the memory 806 may store software for implementing various embodiments of the present invention. The computer system 802 may have additional components. For example, the computer system 802 may include one or more communication channels 808, one or more input devices 810, one or more output devices 812, and storage 814. An interconnection mechanism (not shown) such as a bus, controller, or network, interconnects the components of the computer system 802. In various embodiments of the present invention, operating system software (not shown) provides an operating environment for various softwares executing in the computer system 802 using a processor 804, and manages different functionalities of the components of the computer system 802.

The communication channel(s) 808 allow communication over a communication medium to various other computing entities. The communication medium provides information such as program instructions, or other data in a communication media. The communication media includes, but is not limited to, wired or wireless methodologies implemented with an electrical, optical, RF, infrared, acoustic, microwave, Bluetooth or other transmission media.

The input device(s) 810 may include, but is not limited to, a touch screen, a keyboard, mouse, pen, joystick, trackball, a voice device, a scanning device, or any another device that is capable of providing input to the computer system 802. In an embodiment of the present invention, the input device(s) 810 may be a sound card or similar device that accepts audio input in analog or digital form. The output device(s) 812 may include, but not be limited to, a user interface on CRT, LCD, LED display, or any other display associated with any of servers, desktops, laptops, tablets, smart phones, mobile phones, mobile communication devices, tablets, phablets and personal digital assistants, printer, speaker, CD/DVD writer, or any other device that provides output from the computer system 802.

The storage 814 may include, but not be limited to, magnetic disks, magnetic tapes, CD-ROMs, CD-RWs, DVDs, any types of computer memory, magnetic stripes, smart cards, printed barcodes or any other transitory or non-transitory medium which can be used to store information and can be accessed by the computer system 802. In various embodiments of the present invention, the storage 814 may contain program instructions for implementing any of the described embodiments.

In an embodiment of the present invention, the computer system 802 is part of a distributed network or a part of a set of available cloud resources.

The present invention may be implemented in numerous ways including as a system, a method, or a computer program product such as a computer readable storage medium or a computer network wherein programming instructions are communicated from a remote location.

The present invention may suitably be embodied as a computer program product for use with the computer system 802. The method described herein is typically implemented as a computer program product, comprising a set of program instructions that is executed by the computer system 802 or any other similar device. The set of program instructions may be a series of computer readable codes stored on a tangible medium, such as a computer readable storage medium (storage 814), for example, diskette, CD-ROM, ROM, flash drives or hard disk, or transmittable to the computer system 802, via a modem or other interface device, over either a tangible medium, including but not limited to optical or analogue communications channel(s) 808. The implementation of the invention as a computer program product may be in an intangible form using wireless techniques, including but not limited to microwave, infrared, Bluetooth or other transmission techniques. These instructions can be preloaded into a system or recorded on a storage medium such as a CD-ROM, or made available for downloading over a network such as the Internet or a mobile telephone network. The series of computer readable instructions may embody all or part of the functionality previously described herein.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims. Additionally, the invention illustratively disclose herein suitably may be practiced in the absence of any element which is not specifically disclosed herein and in particular embodiment specifically contemplated, is intended to be practiced in the absence of any element which is not specifically disclosed herein.

The invention claimed is:

1. An apparatus for responding to an apnea condition identified in an infant through non-invasive monitoring of blood analytes, comprising:
 a sensing apparatus configured to detect an apnea condition in an infant, said sensing apparatus comprising:
  a first illumination source—photodetector pair, comprising a first illumination source and a first photodetector, wherein said first photodetector is configured to receive electromagnetic waves that have been emitted from the first illumination source and that have passed through or are reflected off the infant's skin and tissue prior to being received at said first photodetector; and
 a processor configured to determine based on the electromagnetic waves received at least at said first photodetector:
  a first value comprising a peripheral capillary oxygen saturation (SpO2) value corresponding to the infant, wherein said determination of the first value is based on a ratio of (i) reflectance or absorbance readings obtained from infrared spectrum wavelengths, to (ii) reflectance or absorbance readings obtained from red spectrum wavelengths;

a second value comprising a carboxyhaemoglobin (HbCO) value corresponding to the infant, wherein said determination of the second value is based on a ratio of (i) reflectance or absorbance readings obtained from green spectrum wavelengths, to (ii) reflectance or absorbance readings obtained from at least one of red and infrared spectrum wavelengths;

a third value comprising a methaemoglobin (HbMe) value corresponding to the infant, wherein said determination of the third value is based on a ratio of (i) reflectance or absorbance readings obtained from orange spectrum wavelengths, to (ii) reflectance or absorbance readings obtained from at least one of red and infrared spectrum wavelengths;

a fourth value representing a total hemoglobin level of the infant, wherein said fourth value is determined based on the first, second and third values;

a heart rate based on the electromagnetic waves received at said first photodetector; and a respiration rate based on the electromagnetic waves received at said first photodetector;

wherein the processor is configured to detect an apnea condition in an infant based at least on the first value, the heart rate and the respiration rate, and wherein an alarm threshold for such detection is determined based on the fourth value; and a haptic feedback generator configured to stimulate the infant for restoring breathing in response to detection of an apnea condition in the infant, wherein stimulation of the infant is achieved by generating haptic feedback that is sensed by the infant.

2. The apparatus as claimed in claim 1, wherein the fourth value is a sum of (i) the first value multiplied by a first coefficient, (ii) the second value multiplied by a second coefficient and (iii) the third value multiplied by a third coefficient.

3. The apparatus as claimed in claim 1, comprising a second illumination source—photodetector pair, comprising a second illumination source and a second photodetector, wherein said second photodetector is configured to receive electromagnetic waves that have been emitted from the second illumination source and that have passed through an infant's skin and tissue prior to being received at said second photodetector;

wherein the processor is configured to determine a fifth value representing presence of bilirubin in the infant's blood, wherein said fifth value is based on a ratio of (i) reflectance or absorbance readings obtained from blue spectrum wavelengths at the second photodetector, to (ii) reflectance or absorbance readings obtained from at least one of red and infrared spectrum wavelengths received at the first photodetector.

4. The apparatus as claimed in claim 1, wherein the processor is configured to determine a heart rate of the infant based on the electromagnetic waves received at a photodetector within said apparatus, wherein determination of the heart rate is based on a measured elapsed time between received wavelength peaks.

5. The apparatus as claimed in claim 1, wherein the processor is configured to determine a respiratory rate corresponding to the infant, wherein determining said respiratory rate comprises:

converting a reflectance or absorbance waveform received at a photodetector within the apparatus into frequency domain; and determining the infant's respiratory rate based on the frequency and time domain data.

6. The apparatus as claimed in claim 1, wherein:
the infrared spectrum wavelengths include wavelengths between 840 nm to 960 nm;
the red spectrum wavelengths include wavelengths between 550 nm and 690 nm;
the green spectrum wavelengths include wavelengths between 530 nm and 675 nm; and
the orange spectrum wavelengths include wavelengths between 600 nm and 660 nm.

7. The apparatus as claimed in claim 3, wherein the blue spectrum wavelengths include wavelengths between 455 nm and 485 nm.

8. The apparatus as claimed in claim 3, wherein one or more of the red, infrared, green and orange wavelengths are emitted from a first illumination source, and the blue spectrum wavelengths are emitted from a second illumination source.

9. The apparatus as claimed in claim 1, wherein the sensing apparatus comprises one or more of:
one or more thermistors;
a motion detection sensor;
a battery and power management controller; and
a wireless transceiver.

10. The apparatus as claimed in claim 1, wherein said sensing apparatus is configured to adaptively control a number of reflectance or absorbance wavelength samples that are (i) pulsed by illumination source(s) within the sensing apparatus, (ii) received by photodetector(s) within the sensing apparatus and (iii) processed by the processor.

11. The apparatus as claimed in claim 10, wherein the sensing apparatus is configured to modify the number of reflectance or absorbance wavelength samples that are (i) pulsed by illumination source(s) within the sensing apparatus, (ii) received by photodetector(s) within the sensing apparatus and (iii) processed by the processor, based on one or more of:
determination of a distress state or an abnormal state associated with the infant; and
determination of a low charge state associated with a battery within the sensing apparatus.

12. The apparatus as claimed in claim 1, wherein said sensing apparatus is configured such that one or both of red and infrared wavelengths are pulsed by illumination source (s) within the sensing apparatus at a higher frequency than the frequency at which one or more of green, orange and blue wavelengths are pulsed by illumination source(s) within the sensing apparatus.

13. The apparatus as claimed in claim 1, wherein the processor is configured such that determining the first value corresponding to the infant includes data correction of said first value based on data from a motion sensor for removing motion artefacts.

14. A method for responding to an apnea condition identified in an infant through non-invasive monitoring of blood analytes, comprising the steps of:

detecting an apnea condition in an infant by:
receiving at one or more photodetectors, electromagnetic waves that have been emitted from one or more illumination sources and have passed through an infant's skin and tissue prior to being received at said one or more photodetectors; and
based on the electromagnetic waves received at said one or more photodetectors determining at least one of:
a first value comprising a peripheral capillary oxygen saturation (SpO2) value corresponding to the infant, wherein said determination of the first value is based on a ratio of (i) reflectance or absorbance readings obtained from infrared spectrum wavelengths, to (ii) reflectance or absorbance readings obtained from red spectrum wavelengths;

a second value comprising a carboxyhaemoglobin (HbCO) value corresponding to the infant, wherein said determination of the second value is based on a ratio of (i) reflectance or absorbance readings obtained from green spectrum wavelengths, to (ii) reflectance or absorbance readings obtained from at least one of red and infrared spectrum wavelengths;

a third value comprising a methaemoglobin (HbMe) value corresponding to the infant, wherein said determination of the third value is based on a ratio of (i) reflectance or absorbance readings obtained from orange spectrum wavelengths, to (ii) reflectance or absorbance readings obtained from at least one of red and infrared spectrum wavelengths;

a fourth value representing a total hemoglobin level of the infant, wherein said fourth value is determined based on the first, second and third values;

a heart rate based on the electromagnetic waves received at the one or more photodetectors; and a respiration rate based on the electromagnetic waves received at the one or more photodetectors;

wherein detection of an apnea condition in the infant is based at least on the first value, the heart rate and the respiration rate, and wherein an alarm threshold for such detection is determined based on the fourth value; and stimulate the infant for restoring breathing in response to detection of an apnea condition in the infant, wherein stimulation of the infant is achieved by generating through a haptic feedback generator, haptic feedback that is sensed by the infant.

* * * * *